US012718372B2

(12) United States Patent
Shafiee et al.

(10) Patent No.: US 12,718,372 B2
(45) Date of Patent: Aug. 25, 2026

(54) ADAPTIVE NEURAL NETWORKS FOR ANALYZING MEDICAL IMAGES

(71) Applicant: THE BRIGHAM AND WOMEN'S HOSPITAL, INC., Boston, MA (US)

(72) Inventors: Hadi Shafiee, Boston, MA (US); Prudhvi Thirumalaraju, Watertown, MA (US); Manoj Kumar Kanakasabapathy, Boston, MA (US); Sai Hemanth Kumar Kandula, Watertown, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 674 days.

(21) Appl. No.: 18/011,225

(22) PCT Filed: Jun. 29, 2021

(86) PCT No.: PCT/US2021/039718
§ 371 (c)(1),
(2) Date: Dec. 19, 2022

(87) PCT Pub. No.: WO2022/006180
PCT Pub. Date: Jan. 6, 2022

(65) Prior Publication Data

US 2023/0237660 A1 Jul. 27, 2023

Related U.S. Application Data

(60) Provisional application No. 63/166,924, filed on Mar. 26, 2021, provisional application No. 63/045,703, filed on Jun. 29, 2020.

(51) Int. Cl.
*G06K 9/00* (2022.01)
*G06T 7/00* (2017.01)
(Continued)

(52) U.S. Cl.
CPC .......... *G06T 7/0016* (2013.01); *G06V 10/762* (2022.01); *G06V 10/774* (2022.01);
(Continued)

(58) Field of Classification Search
CPC ......... G06T 7/0016; G06T 2207/10056; G06T 2207/20021; G06T 2207/20081;
(Continued)

(56) References Cited

U.S. PATENT DOCUMENTS

2014/0247972 A1 9/2014 Wang et al.
2018/0136451 A1 5/2018 Soenksen
(Continued)

FOREIGN PATENT DOCUMENTS

CN 110736747 A * 1/2020 ........... G06T 7/0012
WO 2018102748 A1 7/2018
WO 2022006180 A1 1/2022

OTHER PUBLICATIONS

Yaroslav Ganin et al: "Domain-adversarial 1-15 training of neural networks", The Journal of Machine Learning Research, vol. 17, May 26, 2016 (May 26, 2016), pp. 1-35, XP002789597, Doi:10.1007/978-3-319-58347-1_10.
(Continued)

*Primary Examiner* — Xin Jia
(74) *Attorney, Agent, or Firm* — Tarolli, Sundheim, Covell & Tummino LLP

(57) ABSTRACT

Systems and methods are provided for medical image classification of images from varying sources. A set of microscopic medical images are acquired, and a first neural network module configured to reduce each of the set of microscopic medical images to a feature representation is generated. The first neural network module, a second neural network module, and a third neural network module are trained on at least a subset of the set of microscopic medical
(Continued)

images. The second neural network module is trained to receive feature representation associated with an image of the microscopic images and classify the image into one of a first plurality of output classes. The third neural network module is trained to receive the feature representation, classify the image into one of a second plurality of output classes based on the feature representation, and provide feedback to the first neural network module.

20 Claims, 2 Drawing Sheets

(51) Int. Cl.

| | |
|---|---|
| ***G06V 10/762*** | (2022.01) |
| ***G06V 10/774*** | (2022.01) |
| ***G06V 10/82*** | (2022.01) |
| ***G06V 20/69*** | (2022.01) |
| ***G16H 50/20*** | (2018.01) |

(52) U.S. Cl.

CPC ............ *G06V 10/82* (2022.01); *G06V 20/698* (2022.01); *G16H 50/20* (2018.01); *G06T 2207/10056* (2013.01); *G06T 2207/20021* (2013.01); *G06T 2207/20081* (2013.01); *G06T 2207/20084* (2013.01); *G06T 2207/30024* (2013.01); *G06V 2201/03* (2022.01)

(58) Field of Classification Search

CPC . G06T 2207/20084; G06T 2207/30024; G06T 7/0012; G06V 10/762; G06V 10/774; G06V 10/82; G06V 20/698; G06V 2201/03; G06V 20/69; G16H 50/20; G06N 3/045; G06N 3/0464; G06N 3/0475; G06N 3/08; G06N 3/0895; G06N 3/09; G06N 3/094; G06N 3/096; G06N 20/00

See application file for complete search history.

(56) References Cited

U.S. PATENT DOCUMENTS

| | | | |
|---|---|---|---|
| 2019/0195874 A1 | 6/2019 | Singhal et al. | |
| 2019/0251330 A1 | 8/2019 | Cotte et al. | |
| 2019/0347467 A1 | 11/2019 | Ohsaka et al. | |
| 2020/0265328 A1* | 8/2020 | Kaditz .................. | G06N 5/046 |
| 2023/0237660 A1 | 7/2023 | Shafiee et al. | |

OTHER PUBLICATIONS

European Search Report dated Apr. 7, 2024 for Application No./ Patent No. 21832127.1-1207/ 4172856 PCT/ US2021039718; Applicant/ Proprietor The Brigham & Women's Hospital, Inc., 10 pages.

Response dated May 3, 2024 to Australian Government Examination Report—Australian Patent Application No. 2021300304 based on PCT Application No. PCT/US2021/039718 Adaptive Neural Networks for Analyzing Medical Images for Applicant The Brigham and Women's Hospital, Inc., dated Jun. 6, 2023, 15 pages.

1st Canadian Office Action for Canadian Patent Application No. 3184293, Applicant The Brigham and Women's Hospital, Inc., dated May 29, 2024, 6 pages.

Office action issued for CA application No. 3,184,293, PCT No. US2021039718, dated Aug. 7, 2025, 5 pages.

Australian Government Examination Report—Australian Patent Application No. 2021300304 based on PCT Application No. PCT/ US2021/039718 Adaptive Neural Networks for Analyzing Medical Images for Applicant The Brigham and Women's Hospital, Inc., dated Jun. 6, 2023, pp. 1-4.

* cited by examiner

ADAPTIVE NEURAL NETWORKS FOR ANALYZING MEDICAL IMAGES

CROSS-REFERENCE TO RELATED APPLICATION

This application claims the benefit of U.S. Provisional Patent Application No. 63/045,703 filed on Jun. 29, 2020, and entitled MOBILE HEALTH (mHEALTH) VIRAL DIAGNOSTICS ENABLED WITH ADAPTIVE ADVERSARIAL LEARNING, and U.S. Provisional Patent Application No. 63/166,924 filed on Mar. 26, 2021 and entitled ARTIFICIAL INTELLIGENCE-BASED METHOD FOR DOMAIN-SHIFTED MEDICAL ANALYSIS. Each of these applications is hereby incorporated by reference in their entirety.

GOVERNMENT LICENSE RIGHTS

This invention was made with government support under grants NIH R01 AI118502, NIH R01A1138800, and NIH R61AI140489 awarded by the National Institutes of Health. The government may have certain rights in the invention

TECHNICAL FIELD

This disclosure relates to clinical decision support systems, and is specifically directed to a real-time intraoperative clinical decision support system.

BACKGROUND

Image analysis, a fundamental component of medical diagnostics, has significantly benefited from human- or super-human levels of feature recognition, anomaly detection, and localization due to advances in supervised deep learning over the past decade. However, supervised learning models, the most widely used deep learning approach in medical image analysis, are often dependent on large expertly annotated datasets and are usually limited to the training data distribution. In medicine, such limitation can have dire consequences where, for example, networks developed using one brand of an instrument can observe drastic drops in performance when tested on data collected using a different brand/instrument of the imaging system used during training. Furthermore, high-quality medical images are critical for human interpreters to annotate, limiting most of the current supervised machine learning approaches to cost-prohibitively expensive state-of-the-art imaging hardware, making the use of these technologies significantly more challenging, particularly in low- and middle-income countries.

SUMMARY

In one example, a method is provided. A set of microscopic medical images are acquired, and a first neural network module configured to reduce each of the set of microscopic medical images to a feature representation is generated. The first neural network module, a second neural network module, and a third neural network module are trained on at least a subset of the set of microscopic medical images. The second neural network module is trained to receive a feature representation associated with an image of the microscopic images and classify the image into one of a first plurality of output classes. The third neural network module is trained to receive the feature representation, classify the image into one of a second plurality of output classes based on the feature representation, and provide feedback to the first neural network module.

In another example, a system includes a processor and a non-transitory computer readable medium, storing executable instructions. The executable instructions include a first neural network module that is configured to receive a microscopic medical image and reduce the image to a feature representation, and a second neural network module that receives the feature representation from the first neural network module and classifies the image into one of a first plurality of classes, each of the first plurality of classes representing one of the medical image sources. Each of the first neural network module and the second neural network module are trained in combination with a third neural network module that is trained on a set of microscopic medical images derived from a plurality of sources to classify the feature representation from the first neural network module into one of a second plurality of classes representing the plurality of sources. The third neural network module provides feedback to the first neural network module representing a performance of the third neural network module.

In a further example, a method is provided. A first set of microscopic medical images associated with at least a first source and a second set microscopic medical images associated with a second source are acquired, and a class of a first plurality of classes to which each of the first set of microscopic medical images belongs is determined. A first neural network module is trained to reduce each of the set of microscopic medical images to a feature representation on the first set of microscopic medical images. The first neural network module, a second neural network module, and a third neural network module are trained on the second set of microscopic medical images. The second neural network module is trained to receive a feature representation associated with an image of the microscopic images and classify the image into one of the first plurality of output classes. The third neural network module is trained to receive the feature representation, classify the image into one of a second plurality of output classes based on the feature representation, and provide feedback to the first neural network module.

BRIEF DESCRIPTION OF THE DRAWINGS

FIG. 3 illustrates a sample dosing window with a dosing alert from an example CDS system.

DETAILED DESCRIPTION

Figure 1:
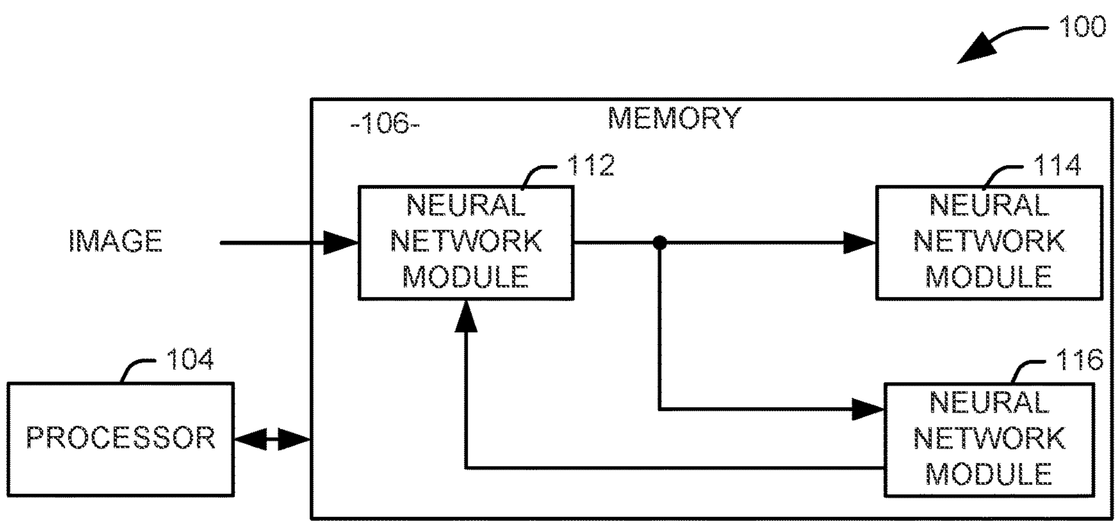
FIG. 1 depicts an example of a system for assigning clinical parameters to medical images that are acquired from varying sources.

As used in this application, "a microscopic medical image" refers to an image, acquired with light in one of the visible, infrared, and ultraviolet spectrums, that represents a characteristic, including the presence or absence of, a biological specimen that cannot be readily viewed by a human eye without assistance. It will be appreciated that a microscopic medical image, as used herein, does not necessarily require that microscopic enhancement be used in acquiring the image, and is intended to cover images containing features visible to the human eye that indirectly reveal characteristics of microscopic biological specimen.

A "source" of an image, as used herein, represents an aspect of the acquisition process for the image that can affect the characteristics of the image used for classifying the image. A given source can include the imaging system or type of imaging system used to acquire the image, a processing step applied to the image, a specific virus or cell type associated with the image, or a similar variation that could result in images from a first source differing substantially from images from a second source despite sharing class membership.

A "clinical parameter," as used herein, is any continuous, ordinal, or categorical parameter that represents a current or predicted future medical condition of a patient, and can include any value representing diagnosis of disease or injury or predicting a patient outcome.

A "range" can have two bounding values (e.g., between five and ten milligrams) or a single explicit bounding value (e.g., less than ten milligrams).

This disclosure relates to systems and methods for providing accurate classification of medical images taken from different sources. Sources, also referred to as domains, can include different institutions with different imaging procedures, different imaging systems, human and animal models, and other differences in the imaging process that might affect the features used for classification. Specifically, the disclosed systems and methods provide a deep learning system for achieving unsupervised domain adaption between various imaging systems in medical image analysis tasks, without the need for any additional domain-specific information including explicit annotations of the domain-shifted images, imaging system's magnifications and fields-of-view, optical and image resolutions, lighting and exposures, and optical image corrections. The system utilizes adversarial learning, a powerful learning technique that is most popular for its generative-variant capable of realistic image synthesis. In the illustrated systems and methods, adversarial learning schemes are employed to refine a neural networks learning process such that common features specific to each target class, across the different domains are prioritized in its decision making. Accordingly, a system can be trained on minimal amounts of annotated data associated with a given source or set of sources and adapted to be accurate for data across a wide variety of sources.

This cross-domain approach allows for reliable performance across varying qualities of data, enabling the use of lower resolution portable imaging systems in classification systems. Specifically, the system can be trained on high quality clinical data and adapted for use on data from portable imaging systems and mobile device-based imaging platforms, greatly expanding the utility of these options, and in some instances, such as the use of mobile device imaging, enabling their use for diagnostic imaging.

FIG. 1 depicts an example of a system 100 for assigning clinical parameters to medical images that are acquired from varying sources 100. In the illustrated example, the system 100 is a classification system, but in practice, the system can be applied to any of segmentation, regression, and object detection tasks as well. In the example of FIG. 1, the system 100 is implemented as one or more processors 104 and a memory 106. It will be appreciated that the memory 106 can comprise one or more discrete units of physical memory operatively connected to process to store data and machine-readable instructions that can be executed by the processor 104. For example, the memory 106 can comprise physical memory, which can reside on the processor 104 (e.g., processor memory), random access memory or other physical storage media (e.g., CD-ROM, DVD, flash drive, hard disc drive, etc.) or a combination of different memory devices that can store the executable instructions. The data utilized for implementing the systems and methods described herein can also be stored in the memory 106 or in some other arrangement of one or more memory structures that are accessible for use by the system 100.

The memory 106 stores a first neural network module 112 with a final flattened layer connected to a second neural network module 114, and a third neural network module 116. The first neural network module 112 can include a plurality of network layers, including various convolutional layers for generating image features as a feature representation at a flattened output layer. The second neural network module 114 can include at least a softmax layer for assigning a given image to a class of a first plurality of classes. The third neural network module 116 can include one or more layers converging to a single node that generates a regularization parameter for use during training. During operation, only the first neural network module 112 and the second neural network module 114 are used to assign clinical parameters to new images by assigning each image to one of a first plurality of classes, with the third neural network module used only during training. Specifically, a novel image is provided to the system, reduced to a feature representation by the first neural network module, and classified into one of the first plurality of classes by the second neural network module to provide the clinical parameter.

During training, the system 100 can utilize either of two different training strategies based on the availability of source data. When annotated data is readily available, that is, when a first set of microscopic medical images having known class membership in one of the first plurality of classes is sufficiently large, the first set of microscopic medical images and a second set of microscopic medical images 120, for which the class membership can be unknown are transformed into feature representations by the first neural network module 112. The feature representations are utilized by the second neural network module 114 and the third neural network 116 module during training. In particular, the second neural network module 114 attempts to classify each image into one of the first plurality of classes to provide the clinical parameter, while the third neural network module 116 attempts to classify each image into one of a second plurality of classes representing the source of the image.

During training, the three modules 112, 114, and 116 are trained by minimizing the classification loss at the second neural network module 114, while maximizing the discriminator loss, or transfer loss, at the third neural network module. The third neural network module 116 is conditioned using the class labels from the first plurality of classes to improve the transfer of class-specific information among data from the various sources. The third neural network module 116, which is trained to discriminate among the second plurality of classes, conditioned by class information for the first plurality of classes, makes use of the class predictions from the second neural network module 114 to compute the conditional distribution.

In one example, to adapt a network trained using a source data distribution $D_s$ for a particular task to a shifted target data distribution $D_t$ for the same task, both $D_s$ and $D_t$ were passed through the first neural network module 112 to iteratively obtain the feature representations $f_s$ and $f_t$ for every data point of $D_s$ and $D_t$. Here, $D_s$ and $D_t$ are represented by $$D_s = \{(X_i^s, Y_i^s)\}_{i=1}^{n_s}$$

and $$D_t = \{(X_j^t)\}_{j=1}^{n_t},$$

where X is the datapoint (image) and Y is the associated classification label for n number of images. A set of features from the flattened layer of the networks first neural network module 112 are used to obtain $f_s$ and $f_t$ from $X^s$ and $X^t$ for every training step. These representations are passed to the classifier block where the conditional probability vectors $c_s$ and $c_t$ are generated using a SoftMax function. The source classifier error at the second neural network module, $\in$(C), is minimized to guarantee lower source risk and is defined as:

$$\varepsilon(C) = \mathbb{E}_{(X_i^s, Y_i^s) \sim D_s} L(C(X_i^s), Y_i^s)$$

where, L( ) represents cross-entropy loss and C( ) is the classifier network.

In parallel, during the adaption process, the discriminator error at the third neural network module 116 is maximized. In the discriminator error calculation, weighted entropy conditioning is utilized along with a multilinear feature map h. The computation of h(f, c) is a multilinear map, formed by the tensor product of feature representation f and classifier prediction c. Where c for k classes is given by $c=[c_1, c_2, c_3 \ldots c_k]$ and f for l dimensions is given by $f=[f_1, f_2, f_3 \ldots f_l]$, respectively. The resultant multilinear map, h is expressed as $$h(f, c) = \begin{bmatrix} f_1 \cdot c_1 & f_1 \cdot c_2 & \ldots & f_1 \cdot c_k \\ f_2 \cdot c_1 & f_2 \cdot c_2 & \ldots & f_2 \cdot c_k \\ f_3 \cdot c_1 & f_3 \cdot c_2 & \ldots & f_3 \cdot c_k \\ \vdots & \vdots & \vdots & \vdots \\ f_l \cdot c_1 & f_l \cdot c_2 & \ldots & f_l \cdot c_k \end{bmatrix}$$

The combination of f and c, performed as a conditioning step, helps preserve class-specific information across data sources. Additionally, entropy can be used as a metric of uncertainty in the classifier predictions to improve the classification performance on data from new sources by encouraging the high confidence predictions in the unlabeled data from the second set of microscopic medical images 120. The uncertainty of the predictions, H(c), was defined as, $$H(c) = -\sum_{i=1}^{n} c_i \log(c_i)$$

Where n is the total number of the first plurality of classes and $c_i$ is the probability vector with each class. Each training example at the third neural network module 116 is weighted with, $$w(H(c)) = 1 + e^{-H(c)}$$

Therefore, the discriminator error E(D) is given by, $$\varepsilon(D) = -\mathbb{E}_{x_i^s \sim D_s} w(H(c_i^s)) \log[D(h_i^s)] - \mathbb{E}_{x_j^t \sim D_t} w(H(c_j^t)) \log[1 - D(h_j^t)]$$

The overall MD-net training is achieved by minimizing source risk and maximizing the discriminator error for distance reduction between the distributions for the various data sources, which is achieved by minimizing the overall cost function given by min (ε(C)−λε(D)), where λ is a selected constant representing tradeoff between discriminator error and source-risk. The stoppage of network training in MD-nets was defined by monitoring performance on source data to minimize overfitting on the target.

Alternatively, where high-quality annotated clinical data is not directly available, the first neural network module 112 can be generated using link weights from another system. In this example, only the unlabeled data from a variety of sources is available. This implementation operates similarly to the implementation described above, but also utilizes an additional frozen feature map extractor (not shown) initialized with the link weights and a clustering element (not shown). Since there is no annotated data available during training, feature maps, $f_{Ts}$, generated by the frozen source feature map extractor are used for training along with pseudo-labels generated by the clustering element when using the unlabeled target data for adaption. The first, second, and third neural network modules 112, 114, and 116 are updated throughout training, and the clustering element is updated periodically at regular intervals, which is treated as a hyperparameter for the different tasks.

The neural network modules 112, 114, and 116 are trained by minimizing the discrepancy between the pseudo-labels generated by the clustering element and the second neural network module, which is treated as the classifier error, ε($C_{nos}$). Additionally, while minimizing the classifier error we maximize the discriminator error at the third neural network module 116. In this approach, during adaption with the unlabeled target examples, the discriminator helps stabilize the adaption process by acting as a regularize, restricting the target feature maps, $f_{Tt}$, in drastically deviating from the frozen source feature maps, $f_{Ts}$.

The classifier error is minimized to match the generated pseudo-labels obtained from the clustering element. For a given set of target images $$X_j^t = [x_1^t, x_2^t, x_3^t \ \ldots\ldots\ldots \ x_j^t],$$

once the initial labels, assigned based on the classifier predictions $$C_{nos}(X_j^t),$$

are assigned, the initial centroids are calculated as:

$$\mu_{k0} = \frac{\sum_{x_{j=1}^t}^{n} C_{nos}(X_j^t) f_{Ts}(X_j^t)}{\sum_{x_{j=1}^t}^{n} C_{nos}(X_j^t)}$$

Once all the centroids for each class are obtained, we compute the initial pseudo-labels, $$\hat{Y}_0^t,$$

by finding the nearest centroid cluster by obtaining the minimum cosine distance between the feature map $$f_{Ts}(X_j^t)$$

and the centroids.

$$\hat{Y}_0^t = \arg\min_k \left\| f_{Tt}(X_j^t) - \mu_{k0}^t \right\|^2$$

Using the generated pseudo-labels, we calculate the centroids and generate pseudo-labels once more, $$\mu_{k1} = \frac{\sum_{x_{j=1}^t}^{n} C_{nos}(X_j^t) f_{Ts}(X_j^t)}{\sum_{x_{j=1}^t}^{n} C_{nos}(X_j^t)}$$

$$\hat{Y}_1^t = \arg\min_k \left\| f_{Tt}(X_j^t) - \mu_{k1}^t \right\|^2$$

The newly generated pseudo-labels are utilized in the calculation of the classifier error during training. The classifier error $\varepsilon(C_{nos})$ is defined as $$\varepsilon(C_{nos}) = \mathbb{E}_{(x_j^t)\sim D_t} L_{nos}\left(c_{nos}(X_j^t), \hat{Y}_1^t\right)$$

where, $L_{nos}(\ )$ represents cross-entropy loss and $C_{nos}(\ )$ is the NoS target classifier network.

Since there are no annotated images, the discriminator error $\varepsilon(D)$ is given by $$\varepsilon(D) = -\mathbb{E}_{x_j^t\sim D_t} w\left(H(c_j^{Ts})\right)\log\left[D(h_j^{Ts})\right] - \mathbb{E}_{x_j^t\sim D_t} w\left(H(c_j^{Tt})\right)\log\left[1 - D(h_j^{Tt})\right]$$

The overall training is achieved similar to the original approach, by minimizing classifier error and maximizing the discriminator error, $\min(\lambda\varepsilon(C_{nos}) - \varepsilon(D))$, where $\lambda$ is a selected constant representing a tradeoff between discriminator error and classifier error.

Data available at different medical clinics can be skewed or may be divergent from the overall distribution due to localization of disease prevalence, practice-dependent technical procedures, variations in the quality and model of data acquisition systems, and variations in patient populations. Since a limitation of most deep learning models is their confinement to the training data domain, the data collected from a single clinical center may not be generalizable across different facilities or instruments. Furthermore, clinical data is highly regulated and thus is not easily available for research or AI-based product development. The development of highly robust machine-learning models that are suitable for multiple centers is, therefore, more difficult due to logistical constraints. While networks can be adapted to different distributions under supervision through additional training using transfer learning with site-specific data, the lack of control on features utilized by the new network may not be well suited for medical image analysis tasks. Such networks would need additional stringent validations that require resources and experts in machine learning and clinical staff, making it difficult for most and impossible for some centers. Even when training using the same dataset, different supervised models, trained identically, tend to perform unpredictably when tested on a shifted distribution. Therefore, although such networks might perform very well during development and initial validation, they may not hold up well when handling shifted or real-world distributions. This problem is likely to worsen with both larger networks and smaller datasets, as is the case with most medical image analysis tasks. The system 100 presents a promising solution for such problems with domain dependence in medical image analysis tasks, where reliability is paramount.

Additional details on example implementations of the system of FIG. 1 can be found in two articles: Kanakasabapathy, M. K., Thirumalaraju, P., Kandula, H. et al. *Adaptive adversarial neural networks for the analysis of lossy and domain-shifted datasets of medical images. Nat Biomed Eng* 5, 571-585 (2021) (available at https://doi.org/10.1038/s41551-021-00733-w) and Shokr A, Pacheco L G C, Thirumalaraju P, Kanakasabapathy M K, Gandhi J, Kartik D, Silva F S R, Erdogmus E, Kandula H, Luo S, Yu X C, Chung R T, Li J Z, Kuritzkes D R, Shafiee H. *Mobile Health (mHealth) Viral Diagnostics Enabled with Adaptive Adversarial Learning. ACS Nano.* 2021 Jan. 26; 15(1):665-673. (available at https://pubs.acs.org/doi/10.1021/acsnano.0c06807). Each of these articles and their supplementary materials are hereby incorporated by reference.

Figure 2:
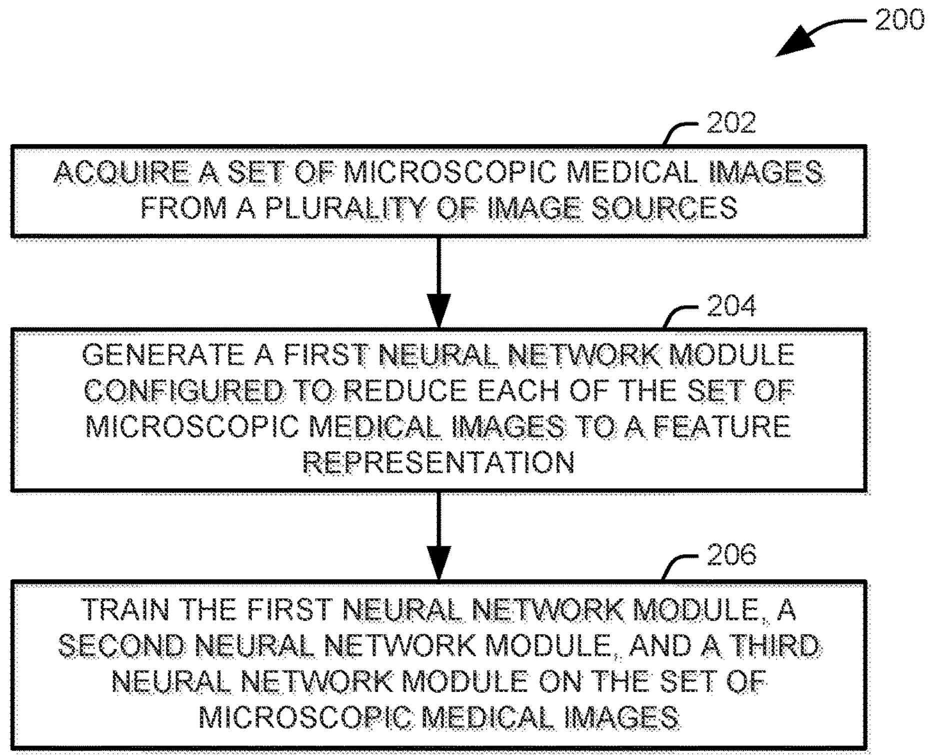
FIG. 2 illustrates an example of a method for training a system for assigning a clinical parameter to a microscopic medical image.
Figure 3:
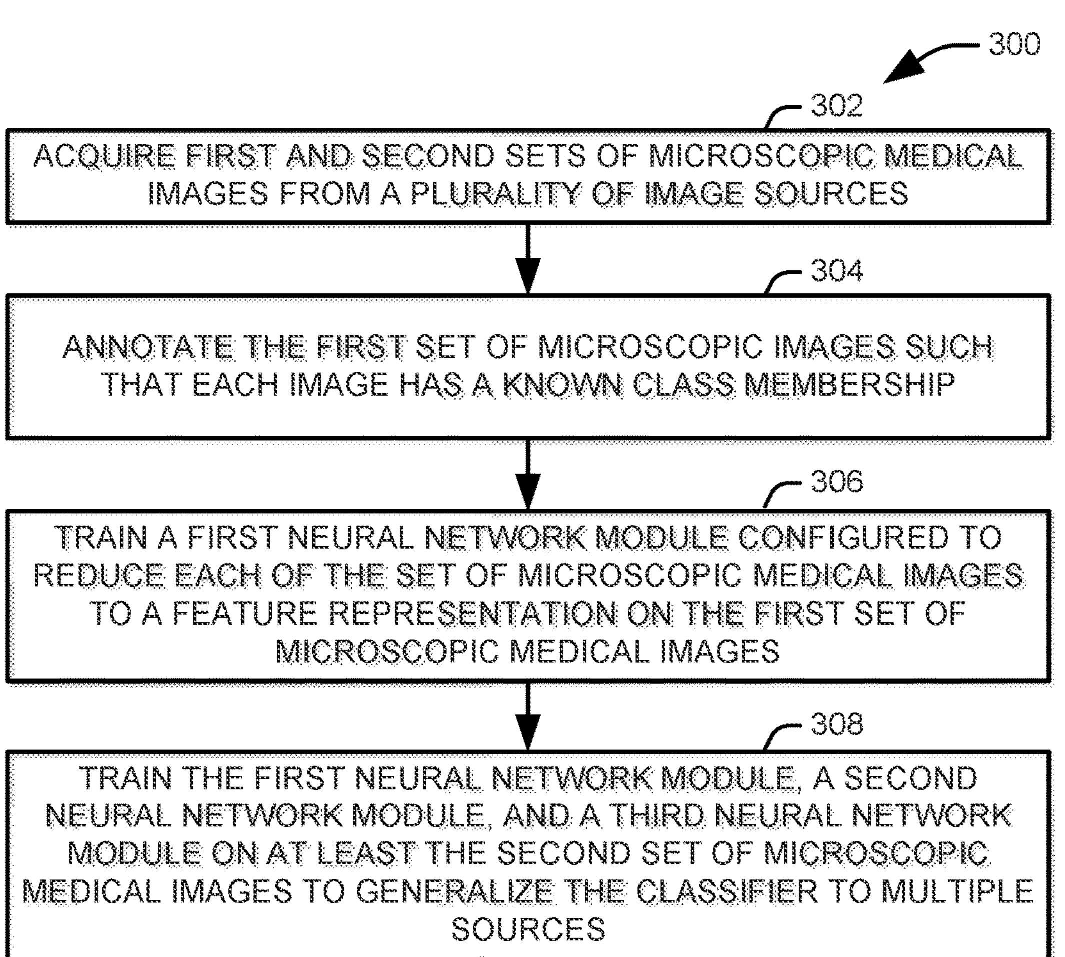
FIG. 3 illustrates another example of a method for training a system for assigning a clinical parameter to a microscopic medical image

In view of the foregoing structural and functional features described above in FIG. 1, example methods will be better appreciated with reference to FIGS. 2 and 3. While, for purposes of simplicity of explanation, the methods of FIGS. 2 and 3 are shown and described as executing serially, it is to be understood and appreciated that the present invention is not limited by the illustrated order, as some actions could in other examples occur in different orders and/or concurrently from that shown and described herein.

FIG. 2 illustrates another example of a method 200 for training a system for assigning a clinical parameter to a microscopic medical image. In particular, the system is trained to classify the image into one of a first plurality of classes and assign a continuous or categorical parameter to the image according to this classification. For example, a categorical parameter can represent the presence or absence of a virus or other pathogen, the morphology of a gamete, the state of development of an embryo, the presence or absence of a disorder, or a predicted patient outcome based on the image. Alternatively, a continuous parameter can represent the likelihood that a virus, pathogen, or other disorder is present, a viral concentration, the likelihood of a patient outcome, the likelihood of success from implanting an imaged embryo or using an imaged sperm for insemination, or similar values.

At 202, a set of microscopic medical images are acquired from a plurality of image sources. In one example, the images are acquired by fabricating nanoprobes using monoclonal antibodies targeting a diagnostic antigen of a given virus on a microfluidic chip, providing a solution containing either the virus or fragments of the virus to the microfluidic chip, and imaging the microfluidic chip after providing the solution to generate the image. A fuel solution can also be provided to ensure that visible signs of the presence of the virus will be detectable. In this implementation, the plurality of image sources each represent a different virus, and the first plurality of classes represent the presence or absence of the virus. The training process of FIG. 2 allows for the system to be trained on annotated samples for a single virus or small batches of annotated samples across multiple viruses, and generalized to a larger population of viruses. While this description focuses on the type of virus, the process could be applied in a similar manner to generalize across a plurality of different animal models and clinical models.

In another example, the set of microscopic medical images are acquired by imaging a set of embryos with various imaging systems. For example, a first subset of the set of microscopic medical images can be captured with a commercial time lapse imaging device, and a second subset of the set of microscopic medical images with a portable imaging device. In this implementation, the first plurality of classes each represent a development state of an embryo of the set of embryos, and the various sources are the imaging systems used to capture the images.

In still another example, a slide containing sperm cells is imaged to produce an image, the image is divided into a set of image tiles, each containing individual cells, and each image tile is provided to a convolutional neural network to determine a subset of the set of image times containing images of sperm cells. In this example, the first plurality of classes can each represent a morphology of the sperm and the sources are the various imaging systems used to image the slides. In a further example, a blood sample from a patient, a slide containing the blood sample is imaged to produce an image, and a template matching algorithm to divide the image into a set of image tiles, each containing individual blood cells. In this example, the first plurality of classes each represent one of the presence and an absence of an infection and the sources are the imaging systems used to image the slides.

At 204, a first neural network module configured to reduce each of the set of microscopic medical images to a feature representation is generated. In one example, the first neural network module is initialized with a set of default weights or assigned random link weights. In another example, link weights from an existing neural network module trained on different microscopic medical images can be provided to the first neural network module. In this example, previous training on the different images can be exploited without the need for the original images original medical data that was used in the development of the network by transferring the link weights to the first neural network module. This is particularly important for medical data because of human data regulations and limitations.

At 206, the first neural network module, a second neural network module, and a third neural network module are trained on at least a subset of the set of microscopic medical images. The second neural network module is trained to receive a feature representation associated with an image of the microscopic images and classify the image into one of a first plurality of output classes. The third neural network module is trained to receive the feature representation, classify the image into one of a second plurality of output classes based on the feature representation, and provide feedback to the first neural network module during training. In practice, the feedback acts as a regularization parameter for the first neural network module discouraging the use if features that are useful for distinguishing among the image sources represented by the second plurality of classes.

In one example, where annotated data is unavailable, the set of microscopic medical images are clustered using a default set of features to generate the first plurality of classes. The training can then be performed, changing the set of features utilized at the first neural network module, and the set of microscopic medical images can be clustered using the new feature set to update the first plurality of classes. In practice, some layers of the first neural network module, and their corresponding sets of link weights can be frozen during training of the first, second, and third neural network modules.

FIG. 3 illustrates another example of a method 300 for training a system for assigning a clinical parameter to a microscopic medical image. At 302, each of a first set of microscopic medical images and a second set of microscopic medical images are acquired. At 304, the first set of microscopic images is annotated such that each image has a known membership in one of the first plurality of classes. In one example, each of the first set of microscopic medical images and the second set of microscopic medical images represent the presence of absence of virus and viral nucleic acids within a microfluidic chip-based assay. Images of the microfluidic chip-based assay can be acquired by any appropriate means, and in one implementation, each image is acquired via a smartphone camera or other portable imaging device, which in some examples, uses a portable optical assembly for magnifying the assay. In one implementation, the first set of microscopic medical images were composed of limited numbers of smartphone-taken photos of microfluidic chip-based assays to specifically detect intact viruses, specifically the hepatitis B virus (HBV), the hepatitis C virus (HCV), human immunodeficiency virus-1 (HIV-1), and severe acute respiratory syndrome coronavirus 2 (SARS-CoV-2), or viral nucleic acids, including those associated with the Zika virus. The second set of microscopic medical images contained a much larger number of unlabeled microchip images, generated using different viral targets and included simulated samples and synthetically generated data.

The microfluidic chip-based assay is configured to consistently generate a simple, non-enzymatic, visual output in a microfluidic chip upon recognition of specific target viral particles or nucleic acids. This visual output could be any colorimetric or fluorescent signals. In one example, the signal is achieved through conjugation of metal nanocatalysts (i.e. platinum nanoparticles, PtNPs) with target-specific recognition antibodies, hereafter referred to as nanoprobes. The images are acquired via capture of the target intact viruses or nucleic acids and on-chip signal generation using nanoprobes and imaging with a smartphone. In the presence of a fuel solution, the catalase-like activity of the PtNPs disproportionates hydrogen peroxide to water and oxygen, then generating a signal output based on oxygen bubbles that can be detected in the microfluidic channel.

The nanoprobes can be fabricated using monoclonal antibodies targeting major diagnostic antigens (AgHBs and HCVcAg) of the hepatitis B and hepatitis C viruses, and also targeting the envelope glycoprotein gp120 of HIV-1. Samples spiked with serial dilutions of laboratory-maintained or commercially available viral strains were then used to standardize on-chip detection assays for these three viruses, providing significant antibody immobilization and high efficiency of virus capture. In a first example implementation, to fabricate specific nanoprobes for different targets, citrate-capped platinum nanoparticles (PtNPs) were conjugated with periodate-oxidized specific monoclonal antibodies, using the heterobifunctional crosslinking reagent 3-[2-Pyridyldithio]propionyl hydrazide (PDPH). Conjugation of the monoclonal antibodies to the PtNPs and functionality of the nanoprobes were confirmed by sodium dodecyl sulfate poly-acrylamide gel electrophoresis, UV-visible spectroscopy, Fourier transform-infrared spectroscopy, $H_2O_2$ decomposition assay, Dynamic Light Scattering and Zeta potential, Transmission Electron Microscopy, and Field-Emission Scanning Electron Microscopy.

In the first example implementation, the assays were prepared from 3.175 mm thick Poly(methyl methacrylate) (PMMA) sheets and double-sided adhesive (DSA) sheets (76 μm, 8213, 3M; or 125 μm, 8215, 3M for SARS-CoV-2), that were cut using a $CO_2$ laser cutter to provide a microfluidic channel as well as microchip inlets and outlets (microchannel dimensions—L: 40 mm; W: 5 mm; H: 0.8 mm). Then, all ethanol-cleaned parts were assembled on glass micro slides previously functionalized for surface immobilization of the virus capture antibodies. Oxygen plasma treatment of the glass surface was done for three minutes, at 100 mTorr, and 20 μl silane-PEG-thiol was added for one hour, followed by ethanol washing. After microchip assembly, specific antibodies (anti-HBV, 45 μg/mL; anti-HCV, 5.2 μg/mL; anti-HIV, 20.4 μg/mL; anti-SARS-CoV-2, 19 μg/mL) previously oxidized and modified with 0.9 mg/mL 3-[2-Pyridyldithio]propionyl hydrazide (PDPH), were incubated in the microchannel for antibody immobilization.

For intact virus detection, 20 μL (HBV, HCV, HIV) or 30 μL (SARS-CoV-2) of plasma or serum sample was incubated in the microchip for twenty minutes (HBV, HCV) or forty-five minutes (HIV, SARS-CoV-2), then the microchannel was washed thoroughly with 0.1 M phosphate buffer (PB) solution). Microchips were incubated with 20 μL of 1:20 specific nanoprobe diluted in phosphate-buffered saline for a further twenty minutes. The nanoprobe solution was then removed and microchips were washed again with PBS. For bubble development, the microchips were filled with 20 μL of a fuel solution comprising six percent hydrogen peroxide and ten percent glycerol, and incubated for ten minutes at room temperature, when photos of bubble development in the microchannels were taken to provide the first set of microscopic medical images.

The CRISPR detection assay relied on using dCas9, associated with a Zika virus (ZIKV) specific single guide RNA, to bind a ZIKV amplified genomic region immobilized on a streptavidin-coated microbead surface. Then, an anti-dCas9 nanoprobe (mAb+PtNPs) was used to detect the dCas9-target nucleic acid association in the microfluidic channel, through bubble formation. Briefly, isolated ZIKV RNA was reverse transcribed to cDNA and amplified using Reverse transcription polymerase chain reaction and biotinylated oligonucleotide primers. For assay standardization, synthetic genomic fragments of ZIKV or Dengue virus (serotypes DENV 1-4) were also used. Following a two minute clean-up step, 10 μL of the amplified products were bound to 10 μL of microbeads, previously washed and resuspended in nuclease-free STE buffer. The microbeads were then incubated with a blocking solution comprising 0.5% Biotin and 5% bovine serum albumin for 20 minutes, before transferring 2.5 μL of the beads solution to a microtube containing a mix of specific sgRNA (100 nM) and dCas9 (100 nM) (in 20 mM HEPES, 5 mM $MgCl_2$, 100 mM NaCl, 0.1 mM EDTA; pre-incubated for fifteen minutes at 37° C. Following further incubation for thirty min at 37° C., and an additional blocking step, microbeads were finally incubated with an anti-Cas9 nanoprobe solution (1:40), washed twice with a 0.05% Triton STE buffer, resuspended in 30 μl of fuel solution, and loaded in the microchip. After fifteen minutes, photos of the bubble development in the microchannel were then taken.

Additional images, which can be used as part of the second set of images, can be generated using simulated virus samples, and all images can be preprocessed to maximize the signal-to-noise ratio. In this example, the images of the microfluidic chips collected using the smartphone camera were cropped to remove the background and isolate the microfluidic channel. Additionally, the channel images are resized to 250×2250 pixels and then split horizontally into three equal parts of size 250×750 pixels. The three parts were tiled adjacently into an image of size 750×750 pixels. The diversity of the data library can also be augmented with images of synthetic data generated using a generative adversarial network model. This allows the library to be expanded without the time and expense necessary to collect and process additional virus samples. In the first example implementation, pre-processed images taken using the smartphone were resized to 256×256 before being provided to the generative adversarial network.

In a second implementation, each of the first set of microscopic medical images and the second set of microscopic medical images represent an embryo. The first set of microscopic medical images comprises images of embryos captured at 113 hours post insemination (hpi) of embryo culture imaged using a commercial time-lapse imaging system. There is no universal grading system for embryos, and the annotators used a five-quality grade system as defined by the Massachusetts General Hospital fertility center which uses a modified Gardener blastocyst grading system. A two-category embryo classification based on the blastocyst status is more commonly recognized worldwide. The two-category system is a condensed version of the five-category system, where two classes of the five-category systems belong to a first class (non-blastocyst) and the other classes belong to a second class (blastocyst). Therefore, images were annotated by embryologists based on their developmental grade, and the annotated data was used for training based on the previously described five-class system focused on embryo morphological features with inferences made at a two-class level.

In the second example implementation, the second set of microscopic medical images comprises embryo images from a number of sources. One set of images are recorded using various clinical benchtop microscopes under bright field illumination. Another set of images was generated using a portable stand-alone imaging system that consists of a single-board computer, an LED, a complementary metal-oxide-semiconductor (CMOS) sensor, and a 10× achromatic objective lens. A third set of images were acquired via a smartphone-based optical system. Specifically, an optical attachment interfaces with a smartphone and houses a plano-convex lens, a coin battery, and an LED. The plano-convex lens is positioned inside the optical attachment such that it aligns with the optical axis of the smartphone's front camera. Embryos were illuminated by the battery-powered LED, and sample fine focus was achieved through the smartphone's autofocus capability.

In a third example implementation, each of the first set of microscopic medical images and the second set of microscopic medical images represent a sperm cell. The first set of microscopic medical images can be obtained from images of slides of smeared and stained human sperm samples using 100× microscopes. The resolution of these images in their stitched form can be as high as 266,000×180,000 pixels. Individual cells are identified within each sample during preprocessing, and image times containing individual cells are provided to a convolutional neural network to determine if they are sperm cells or non-sperm cells. Individual sperm image annotations used four classes representing normal sperm, head defects, neck defects, and tail defects. The sperm image data used for the second set of microscopic medical images were obtained from imaging smeared semen samples on glass slides and stained using the Romanowsky staining method. A first set of images were recorded using a benchtop Keyence microscope at 60× magnification, a second set was recorded using a 3D-printed portable imaging system similar to the system used in the second example implementation, and a third set was recorded using a 3D-printed smartphone-based imaging system similar to that used in the second example implementation.

In a fourth example implementation, each of the first set of microscopic medical images and the second set of microscopic medical images represent a blood cell. The first set of microscopic images can be acquired from thin-blood smear slides which were collected from *P. falciparum*-infected patients and healthy controls. The thin-smear slides were imaged using a smartphone camera attached to a benchtop brightfield microscope, and segmentation was performed to isolate individual red blood cell images. All images were manually annotated between infected (parasitized) and non-infected (non-parasitized) cells by an expert slide reader. The second set of microscopic medical images were acquired in three sets, with one acquired using a benchtop microscope, a second acquired using a portable stand-alone 3D-printed microscope similar to that described for the embryo implementation, and a third acquired using a smartphone-based microscope similar to that described for the embryo implementation. Individual cells were extracted from these images using a template matching algorithm.

At 306, a first neural network module configured to reduce each of the set of microscopic medical images to a feature representation is trained on the first set of microscopic medical images. This allows for a preliminary extraction of a feature representation for each image that is relevant to distinguishing among the first plurality of classes, although it is tied to characteristics of the source associated with the first set of microscopic medical images. At 308, the first neural network module, a second neural network module, and a third neural network module on at least the second set of microscopic medical images to generalize the system formed by the three neural network modules to multiple sources.

During this training, the second neural network module is trained to receive a feature representation associated with an image of the microscopic images from the first neural network module and classify the image into one of the first plurality of output classes to provide the clinical parameter. The third neural network module is trained to receive the feature representation, classify the image into one of a second plurality of output classes based on the feature representation, and provide feedback to the first neural network module. Each of the second plurality of output classes represent one of a plurality of sources associated with the second set of microscopic medical images. Accordingly, the performance of the third neural network module represents the ability of the first neural network module to produce features that distinguish among images from the various sources. By penalizing such features during training, the first neural network module is forced to generate features that generalize across sources.

Figure 4:
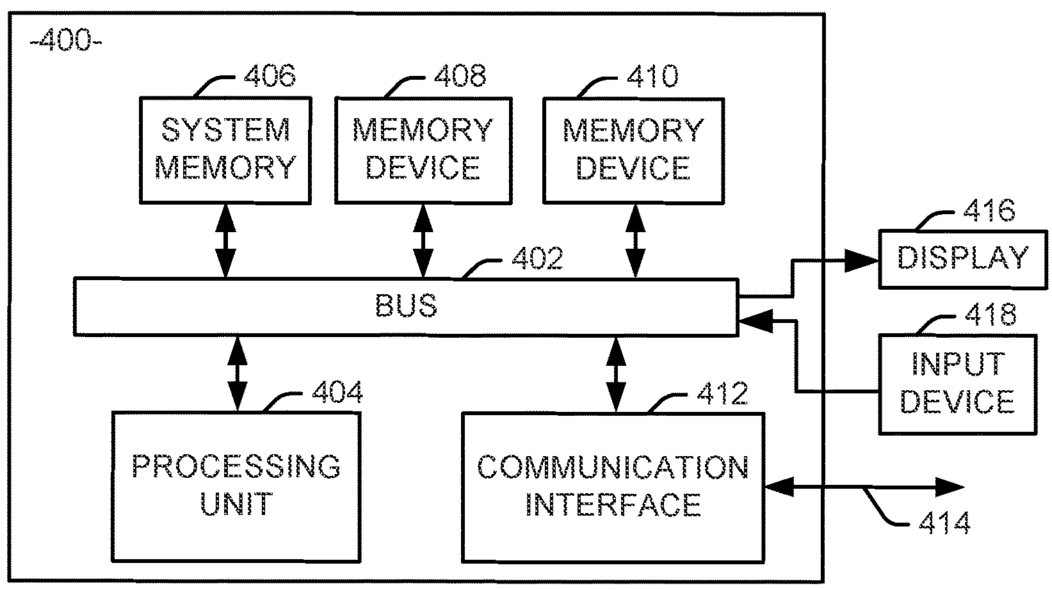
FIG. 4 is a schematic block diagram illustrating an exemplary system of hardware components capable of implementing examples of the systems and methods disclosed in FIGS. 1-3.

FIG. 4 is a schematic block diagram illustrating an exemplary system 400 of hardware components capable of implementing examples of the systems and methods disclosed in FIGS. 1-3. The system 400 can include various systems and subsystems. The system 400 can be a personal computer, a laptop computer, a workstation, a computer system, an appliance, an application-specific integrated circuit (ASIC), a server, a server blade center, a server farm, etc.

The system 400 can includes a system bus 402, a processing unit 404, a system memory 406, memory devices 408 and 410, a communication interface 412 (e.g., a network interface), a communication link 414, a display 416 (e.g., a video screen), and an input device 418 (e.g., a keyboard and/or a mouse). The system bus 402 can be in communication with the processing unit 404 and the system memory 406. The additional memory devices 408 and 410, such as a hard disk drive, server, stand-alone database, or other non-volatile memory, can also be in communication with the system bus 402. The system bus 402 interconnects the processing unit 404, the memory devices 406-410, the communication interface 412, the display 416, and the input device 418. In some examples, the system bus 402 also interconnects an additional port (not shown), such as a universal serial bus (USB) port.

The processing unit 404 can be a computing device and can include an application-specific integrated circuit (ASIC). The processing unit 404 executes a set of instructions to implement the operations of examples disclosed herein. The processing unit can include a processing core.

The additional memory devices 406, 408, and 410 can store data, programs, instructions, database queries in text or compiled form, and any other information that can be needed to operate a computer. The memories 406, 408 and 410 can be implemented as computer-readable media (integrated or removable) such as a memory card, disk drive, compact disk (CD), or server accessible over a network. In certain examples, the memories 406, 408 and 410 can comprise text, images, video, and/or audio, portions of which can be available in formats comprehensible to human beings. Additionally or alternatively, the system 400 can access an external data source or query source through the communication interface 412, which can communicate with the system bus 402 and the communication link 414.

In operation, the system 400 can be used to implement one or more parts of an image classification system in accordance with the present invention. Computer executable logic for implementing the image classification system resides on one or more of the system memory 406, and the memory devices 408, 410 in accordance with certain examples. The processing unit 404 executes one or more computer executable instructions originating from the system memory 406 and the memory devices 408 and 410. The term "computer readable medium" as used herein refers to any medium that participates in providing instructions to the processing unit 404 for execution, and it will be appreciated that a computer readable medium can include multiple computer readable media each operatively connected to the processing unit.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to portable or fixed storage devices, optical storage devices, wireless channels, and/or various other storage mediums capable of storing that contain or carry instruction(s) and/or data.

What have been described above are examples of the invention. It is, of course, not possible to describe every conceivable combination of components or methodologies, but one of ordinary skill in the art will recognize that many further combinations and permutations of the invention are possible. Accordingly, the invention is intended to embrace all such alterations, modifications and variations that fall within the scope of the appended claims and the application. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. A method comprising:

acquiring a set of microscopic medical images;

generating a first neural network module configured to reduce each of the set of microscopic medical images to provide a plurality of feature representations; and training the first neural network module, a second neural network module, and a third neural network module in a training process on at least a subset of the set of microscopic medical images, wherein the second neural network module is trained to receive a first feature representation of the plurality of feature representations, representing a first image of the microscopic images and classify the first image into one of a first plurality of output classes and the third neural network module is trained to receive the first feature representation, classify the first image into one of a second plurality of output classes based on the first feature representation, and provide feedback to the first neural network module, the third neural network module operating only during the training process.

2. The method of claim 1, wherein the set of microscopic medical images is a first set of microscopic medical images and generating the first neural network module comprises:

training a fourth neural network module on a second set of microscopic medical images to generate a set of link weights; and providing the set of link weights to the first neural network module.

3. The method of claim 1, further comprising:

clustering the set of microscopic medical images using a default set of features to generate the first plurality of classes;

training each of the first neural network module, the second neural network module, and the third neural network module on the set of microscopic medical images to discriminate among the first plurality of classes, a set of link weights of the first neural network module defining a new feature set; and clustering the set of microscopic medical images using the new feature set to update the first plurality of classes.

4. The method of claim 3, wherein the first neural network module comprises at least two sets of link weights, at least one of the sets of link weights being frozen during training of the first neural network module, the second neural network module, and the third neural network module.

5. The method of claim 1, wherein acquiring a given image of the set of microscopic medical images comprises:

fabricating nanoprobes using monoclonal antibodies targeting a diagnostic antigen of a given virus on a microfluidic chip;

providing a solution containing one of the given virus or fragments of the given virus to the microfluidic chip; and imaging the microfluidic chip after providing the solution to generate the image.

6. The method of claim 5, wherein the first plurality of classes represent the presence or absence of the virus.

7. The method of claim 1, wherein acquiring the set of microscopic medical images comprises imaging a set of embryos, a first embryo of the set of embryos being imaged with a first imaging system and a second embryo of the set of embryos being images with a second imaging system.

8. The method of claim 7, wherein the first plurality of classes each represent a development state of an embryo of the set of embryos and the second plurality of classes represent the imaging system used to capture a given image.

9. The method of claim 1, wherein acquiring the set of microscopic medical images comprises acquiring a first subset of the set of microscopic medical images with an imaging device that produces images having a first quality, and acquiring a second subset of the set of microscopic medical images with a portable imaging device having a second resolution that is less or equal to than the first quality.

10. The method of claim 1, wherein acquiring the set of microscopic medical images comprises:

imaging a slide containing sperm cells to produce an image;

dividing the image into a set of image tiles, each containing individual cells; and providing each image tile of the set of image tiles to a convolutional neural network to determine a subset of the set of image times containing images of sperm cells, the set of microscopic medical images comprising the subset of the set of image tiles.

11. The method of claim 10, wherein the first plurality of classes each represent a morphology of the sperm and the second plurality of classes represent the imaging system used to image the slide.

12. The method of claim 10, wherein the first plurality of classes each represent one of the presence and an absence of an infection and the second plurality of classes represent the imaging system used to image the slide.

13. The method of claim 1, wherein acquiring the set of microscopic medical images comprises:

drawing a blood sample from a patient;

imaging a slide containing the blood sample to produce an image; and applying a template matching algorithm to divide the image into a set of image tiles, each containing individual blood cells, the set of microscopic medical images comprising the subset of the set of image tiles.

14. The method of claim 1, wherein acquiring the set of microscopic medical images comprises:

acquiring a first set of microscopic medical images associated with at least a first source;

determining a class of the first plurality of classes to which each of the first set of microscopic medical images belongs; and acquiring a second set of microscopic medical images associated with at least a second source.

15. The method of claim 14, wherein generating the first neural network module comprises training the first neural network module and the second neural network module on the first plurality of images, and training the first neural network module, the second neural network module, and the third neural network module comprises training the first neural network module, the second neural network module, and the third neural network module on at least the second set of microscopic medical images.

16. A system comprising:

a processor;

a non-transitory computer readable medium, storing executable instructions, the executable instructions comprising:

a first neural network module that is configured to receive a microscopic medical image and reduce the image to a feature representation;

a second neural network module that receives the feature representation from the first neural network module and classifies the image into one of a first plurality of classes, each of the first plurality of classes representing one of the medical image sources;

wherein each of the first neural network module and the second neural network module are trained in combination with a third neural network module that is trained on a set of microscopic medical images derived from a plurality of sources to classify the feature representation from the first neural network module into one of a second plurality of classes representing the plurality of sources, the third neural network module operating only during the training process to provide feedback to the first neural network module representing a performance of the third neural network module.

17. The system of claim 16, wherein the first neural network module comprises a plurality of sets of link weights, with a first set of link weights of the plurality of sets of link weights being held constant when the first neural network module and the second neural network module are trained in combination with a third neural network module.

18. The system of claim 16, further comprising a clustering element that clusters the set of microscopic medical images according to a set of features associated with the first neural network module to provide the first plurality of classes, the clustering element updating the first plurality of classes periodically while the first neural network module and the second neural network module are trained in combination with a third neural network module.

19. A method comprising:

acquiring a first set of microscopic medical images associated with at least a first source;

determining a class of a first plurality of classes to which each of the first set of microscopic medical images belongs; and acquiring a second set of microscopic medical images associated with at least a second source;

training a first neural network module on the first set of microscopic medical images to reduce a given microscopic medical image to a corresponding feature representation; and training the first neural network module, a second neural network module, and a third neural network module on the second set of microscopic medical images, wherein the second neural network module is trained to receive a feature representation associated with an image of the second set of microscopic images and classify the image into one of the first plurality of output classes, and the third neural network module is trained to receive the feature representation, classify the image into one of a second plurality of output classes based on the feature representation, and provide a regularization parameter as feedback to the first neural network module.

20. The method of claim 19, wherein the second plurality of classes includes a first class representing the first source and a second class representing the second source.

* * * * *